United States Patent
Laurie et al.

(10) Patent No.: US 10,729,772 B2
(45) Date of Patent: *Aug. 4, 2020

(54) TRACE ELEMENTS

(71) Applicant: WARBURTON TECHNOLOGY LIMITED, Dublin (IE)

(72) Inventors: Robert Naylor Laurie, Somerset West (ZA); William Alfred Smith, Porterville, CA (US)

(73) Assignee: WARBURTON TECHNOLOGY LIMITED, Dublin (IE)

( * ) Notice: Subject to any disclaimer, the term of this patent is extended or adjusted under 35 U.S.C. 154(b) by 30 days.

This patent is subject to a terminal disclaimer.

(21) Appl. No.: 16/148,467

(22) Filed: Oct. 1, 2018

(65) Prior Publication Data

US 2019/0030164 A1    Jan. 31, 2019

Related U.S. Application Data

(60) Continuation of application No. 11/861,724, filed on Sep. 26, 2007, now Pat. No. 10,183,075, which is a division of application No. 10/834,094, filed on Apr. 29, 2004, now Pat. No. 7,285,292.

(51) Int. Cl.

| | | |
|---|---|---|
| *A61K 33/26* | (2006.01) | |
| *A61K 33/32* | (2006.01) | |
| *A61K 33/04* | (2006.01) | |
| *A61K 31/28* | (2006.01) | |
| *A61K 33/00* | (2006.01) | |
| *A61K 33/24* | (2019.01) | |
| *A61K 33/30* | (2006.01) | |
| *A61K 33/34* | (2006.01) | |
| *A61K 45/06* | (2006.01) | |

(52) U.S. Cl.
CPC .............. *A61K 45/06* (2013.01); *A61K 31/28* (2013.01); *A61K 33/00* (2013.01); *A61K 33/04* (2013.01); *A61K 33/24* (2013.01); *A61K 33/26* (2013.01); *A61K 33/30* (2013.01); *A61K 33/32* (2013.01); *A61K 33/34* (2013.01); *Y10S 424/06* (2013.01); *Y10S 514/836* (2013.01)

(58) Field of Classification Search
CPC ........ A61K 31/28; A61K 33/00; A61K 33/04; A61K 33/24; A61K 33/26; A61K 33/30; A61K 33/32; A61K 33/34; A61K 45/06
See application file for complete search history.

(56) References Cited

U.S. PATENT DOCUMENTS

| | | | | |
|---|---|---|---|---|
| 7,285,292 B2 * | 10/2007 | Laurie | ................... | A61K 31/28 424/634 |
| 8,377,482 B2 * | 2/2013 | Laurie | .................. | A61K 31/095 424/634 |
| 10,183,075 B2 * | 1/2019 | Laurie | ................... | A61K 31/28 |
| 2002/0068079 A1 * | 6/2002 | Laurie | .................. | A61K 9/0019 424/422 |

OTHER PUBLICATIONS

The European Agency for the Evaluation of Medicinal Products, Committee for Veterinary Medicinal Products, Summary Report. Chlorocresol [online], pp. 1-3, Mar. 1996 [retrieved on Jan. 18, 2007]. Retrieved from the Internet: <URL: http://emea.eu.int/pdfs/vet/mrls/007496en.pdf >.*
McDowell, L.R. et al., "Mineral supplementation of beef cattle in the Bolivian Tropics," Journal of Animal Science, vol. 55, pp. 964-970 (1982).*
VETU abstract 1993-63594 (1993).*

* cited by examiner

*Primary Examiner* — John Pak
(74) *Attorney, Agent, or Firm* — Stephen J. Weyer, Esq.; Stites & Harbison, PLLC

(57) ABSTRACT

A trace element solution comprises selenium, zinc, manganese and iron at a concentration of at least 60 mg/ml. The solution may further comprise at least one compound selected from the group comprising iodine, potassium iodide, sodium iodide, iron chloride, zinc oxide, manganese sulphate, sodium selenite, copper carbonate, sodium carbonate, anhydrous disodium EDTA and sodium hydroxide.

13 Claims, No Drawings

TRACE ELEMENTS

CROSS REFERENCE TO RELATED APPLICATIONS

This application is a continuation of U.S. patent application Ser. No. 11/861,724, which in turn is a divisional of Application Ser. No. 10/834,094, filed Apr. 29, 2004, and issued as U.S. Pat. No. 7,285,292, all herein incorporated by reference.

FIELD OF INVENTION

The present invention relates to trace elements.

BACKGROUND TO INVENTION

It has been found that there is a deficiency of certain trace elements in pastures for livestock in particular areas around the world. Various suggestions have been made to provide the required trace elements to such animals. Different chemical compounds and complexes have been investigated for applying the trace elements by way of licks, drenches or injections.

In general the problem with injectable solutions is that there are too low concentrations of the minerals in the solutions. This means that relatively large quantities have to be injected, which in turn causes tissue damage and also abscesses at the site of injection. Furthermore, it is generally the case that different trace elements seldomly are individually sufficient. This means that two or more trace element solutions have to be provided by way of separate injections.

ZA 1982/6778 (Laurie) discloses a trace element solution and a method of providing the trace elements to livestock. These trace element solution include ethylene diamino tetra acetic acid complex of the required mineral in suitable quantities. However, the trace element solution includes no selenium or selenite compound.

In the specification and claims the expression EDTA refers to ethylene diaminotetraacetic acid ($C_{10}H_{16}O_8N_2$ or ($HO_2CH_2C)_2NCH_2CH_2N$—$(CH_2CO_2H)_2$). U.S. Pat. No. 4,335,116 (Howard) discloses mineral-containing therapeutic compositions containing EDTA complexes of trace elements. Notably, U.S. Pat. No. 4,335,116 utilizes tetra-sodium EDTA, a selenium glycine complex, and metal chlorides for the preparation of the EDTA complexes. Unfortunately, the chloride ions cause contamination and each complex solution is to be made individually. Furthermore, overnight time is required for complexing and heating up afterward to speed up the process, requires extra apparatus. If mixtures are required, the individual solutions are to be blended. If various concentrations as well as compositions are to be made, it can only be done in a cumbersome way, requiring extra apparatus. A further problem may arise when mixtures of high concentration are needed. In certain cases it would be impossible to deliver them, because mixing is always accompanied by dilution.

U.S. Pat. No. 6,638,539 (Laurie et al) discloses a method of preparing a trace element solution, which includes the steps of providing at least one EDTA-complex, of providing a sodium selenite solution, and of combining the EDTA-complexes and the sodium selenite solution. However, the method enables production of a trace element solution of only about 55 mg/ml.

It is an object of the invention to suggest methods and means for overcoming these problems.

SUMMARY OF INVENTION

According to the invention, a trace element solution, which comprises selenium, copper, zinc, manganese and iron at a concentration of at least 60 mg/ml.

The solution may comprise one or more of the following: iodine, potassium iodide, sodium iodide, iron chloride, zinc oxide, manganese sulphate, sodium selenite, copper carbonate, sodium carbonate, anhydrous disodium EDTA and sodium hydroxide.

At least one of the metal(s) may be provided in the form of an EDTA complex.

The EDTA complex may be obtained by means of at least one compound selected from the group comprising sodium EDTA and potassium EDTA.

The solution may comprise chlorocresol as preservative.

The solution may be prepared in a continuous batch process.

The solution may be an injectable solution.

The solution may be a drenchable solution.

Also according to the invention, a method of preparing a trace element solution comprising at least one metal selected from the group comprising selenium, copper, zinc, manganese and chromium and comprising a concentration of the metal(s) of at least 60 mg/ml, said method consisting essentially of the steps of:

(a) preparing a $MnCO_3$ mixture in a container;
(b) adding an EDTA solution to the container and subsequently adding at least one metal compound; and
(c) adding $Na_2SeO_3$ to the container to obtain the trace element solution.

The EDTA solution may be selected from the group comprising a potassium EDTA solution and a sodium EDTA solution.

The method may comprise the step of adding $CrCl_3.6H_2O$ to the trace element solution.

The method may comprise the step of adding a EDTA/NaOH mixture prior to addition of the $CrCL_3.6H_2O$ to the trace element solution.

The method may comprise the step of adjusting the pH of the trace element solution to 6.7 to 7.0.

The method may comprise the step of adjusting the pH of the trace element solution by adding at least one compound selected from the group comprising NaOH and EDTA.

The trace element solution may be diluted.

The temperature of the $MnCO_3$ mixture may be at least 60 degrees Celsius.

Water having a temperature of at least 70 degrees Celsius may be added to the $MnCO_3$ mixture.

The addition of the EDTA/NaOH mixture may occur gradually with small quantities.

The method may comprise the step of cooling the trace element solution prior to addition of the $Na_2SeO_3$.

The $MnCO_3$ mixture may be prepared by mixing $MnSO_4$ and $Na_2CO_3$.

The metal compound may be selected from the group comprising $ZnO$, $CuCO_3$, $Na_2CO3$, $MnSO_4$ and $FeCl_3$.

The metal compound may be selected from the group comprising metal oxides, metal hydroxides and metal carbonates.

Yet further according to the invention, a trace element solution as prepared by the above method.

Yet further according to the invention, a stock lick, which comprises a trace element solution as prepared by the method above.

Yet further according to the invention, a method of providing trace elements to animals, such as livestock, which comprises the steps of preparing a trace element solution as described above and of providing the solution in a suitable quantity to an animal.

Yet further according to the invention, an injectable trace element solution, which comprises at least one compound selected from the group comprising iodine, potassium iodine and sodium iodine and which comprises a concentration of the compound(s) of at least 20 mg/ml.

Yet further according to the invention, a trace element solution, which comprises at least one compound selected from the group comprising chromium and $CrCl_3.6H_2O$.

Yet further according to the invention, a trace element solution, which
(a) comprises at least one metal selected from the group comprising selenium, copper, zinc, manganese and chromium;
(b) comprises a concentration of the metal(s) of at least 60 mg/ml,
(c) comprises at least one of the metal(s) provided in the form of an EDTA complex; and
(d) which is obtained by at least one compound selected from the group comprising iodine, potassium iodide, sodium iodide, iron, iron chloride, zinc oxide, manganese sulphate, sodium selenite, copper carbonate, sodium carbonate, anhydrous disodium EDTA and sodium hydroxide.

Yet further according to the invention, a method of preparing a trace element solution comprising at least one metal selected from the group comprising selenium, copper, zinc, manganese and chromium and comprising a concentration of the metal(s) of at least 60 mg/ml, said method consisting essentially of the steps of:
(a) preparing a $MnCO_3$ mixture in a container at a temperature of at least 60 degrees Celsius;
(b) adding an EDTA solution to the container and subsequently adding at least one metal compound selected from the group comprising ZnO, $CuCO_3$, $Na_2CO_3$, $MnSO_4$ and $FeCl_3$;
(c) adding at least one compound selected from the group comprising $Na_2SeO_3$ and $CrCl_3.6H_2O$ to the container to obtain the trace element solution; and
(d) adjusting the pH of the trace element solution.

Yet further according to the invention, a trace element solution, which comprises
(a) 35-50 mg/ml of zinc;
(b) 10-15 mg/ml manganese;
(c) 5-10 mg/ml selenium; and
(d) 10-20 mg/ml copper.

The solution may comprise 5-10 mg/ml chromium.
The solution may comprise 5-50 mg/ml iron.
The solution may comprise 20-400 mg/ml iodine.

DESCRIPTION OF EXAMPLES

The invention will now be described by way of example of injectable solutions in accordance with the invention.

Example 1

Example 1 relates to a method to prepare a trace element solution predominantly to be used for cattle and includes the mineral elements selenium, copper and chromium.

The method enables preparation of 25 litres of the solution containing 40 mg Zn, 10 mg Mn, 5 mg Se, 15 mg Cu and 5 mg Cr per ml.

A. Preparing $MnCO_3$

In a suitable container/drum, the $MnCO_3$ mud is prepared by adding solutions of 900 g $MnSO_4$ and 1150 g $Na_2CO_3$ together. The resultant mixture is decanted and washed three times.

B. Continuous Batch Process

To the $MnCO_3$ mud, hot water (70° C.) is added to a volume of at least 15 litres. Critical is the temperature at the start of the batch process which should be at least 60° C.

B.1 Preparing MnEDTA 2000 g EDTA and 500 g NaOH are weighed; the EDTA and NaOH are mixed; the EDTA/NaOH mixture is added to the drum, in small quantities to prevent excessive frothing, until the reaction is complete (leaving a clear pinkish solution).

B.2 Preparing ZnEDTA (2 steps)

Step 1:
2600 g EDTA, 690 g NaOH and 700 g ZnO are weighed, the EDTA and NaOH are mixed and ZnO is kept separate. The EDTA/NaOH mixture is added to the drum in small quantities to prevent boiling over, followed by addition of the ZnO. The reaction is allowed to complete (again leaving a clear pink solution). The temperature at this stage could reach 103° C.

Step 2:
2600 g EDTA, 690 g NaOH and 700 g ZnO are weighed. The EDTA and NaOH are mixed and the ZnO kept separate. The EDTA/NaOH mixture is added to the drum in small quantities to prevent boiling over, where after the ZnO is added. The reaction is allowed to complete (again leaving a clear pink solution). The temperature at this stage could reach 103° C.

B.3 Preparing CuEDTA 1760 g EDTA, 462 g NaOH and 693 g basic $CuCO_3$ are weighed. The EDTA and NaOH are mixed and the $CuCO_3$ kept separate. The EDTA/NaOH mixture is added to the drum, followed by careful addition of the $CuCO_3$, to prevent excessive frothing, and the reaction is allowed to complete (leaving a clear blue solution).

B.4 25 g chlorocresol is added and stirred till dissolved.
B.5 23 litres is made up
B.6 The mixture is allowed to cool to room temperature.

C. Final Phase

C.1 303 g $Na_2SeO_3$ is added.
C.2 The pH is adjusted to 6,7 by adding NaOH (40% solution) or EDTA.
C.3 738 g EDTA, 192 g NaOH and 641 g $CrCl_3.6H_2O$ are weighed. The EDTA and NaOH are mixed and added to the drum. The $CrCl_3.6H_2O$ is added, whereby the reaction is slow.
C.4 The volume is made up to 25 litres.

Example 2

Example 2 relates to a method to prepare a trace element solution predominantly to be used for sheep and includes the mineral elements Selenium and Copper.

The method enables preparation of 100 litres of the solution containing 40 mg Zn, 10 mg Mn, 3 mg Se and 10 mg Cu per ml.

A. Preparing MnCO₃

In a suitable container/drum, the MnCO₃ mud is prepared by adding solutions of 3600 g MnSO₄ and 4600 g Na₂CO₃ together. The mixture is decanted and wash three times.

B. Continuous Batch Process

To the MnCO₃ mud, is added hot water (70° C.) to a volume of at least 60 litres. The temperature at the start of the batch process is critical and should be at least 60° C.

B.1 Preparing MnEDTA 8000 g EDTA and 2000 g NaOH are weighed. The EDTA and NaOH are mixed. The EDTA/NaOH mixture is added to the drum, in small quantities to prevent excessive frothing, until the reaction is complete (leaving a clear pinkish solution).

B.2 Preparing ZnEDTA (2 steps)

Step 1:

10400 g EDTA, 2760 g NaOH and 2800 g ZnO are weighed. The EDTA and NaOH are mixed and the ZnO kept separate. The EDTA/NaOH mixture is added to the drum in small quantities to prevent boiling over, followed by addition of the ZnO. The reaction is allowed to complete (again leaving a clear pink solution). The temperature at this stage could reach 103° C.

Step 2:

10400 g EDTA, 2760 g NaOH and 2800 g ZnO are weighed. The EDTA and NaOH are mixed and the ZnO kept separate. The EDTA/NaOH mixture is added to the drum in small quantities to prevent boiling over, followed by addition of the ZnO. The reaction is allowed to complete (again leaving a clear pink solution). The temperature at this stage could reach 103° C.

B.3 Preparing CuEDTA 4646 g EDTA, 1220 g NaOH and 1835 g basic CuCO₃ are weighed. The EDTA and NaOH are mixed and the CuCO₃ kept separate. The EDTA/NaOH mixture is added to the drum, followed by careful addition of the CuCO₃, to prevent excessive frothing, and the reaction is allowed to complete (leaving a clear blue solution).

B.4 100 g chlorocresol is added and the mixture stirred until dissolved.

B.5 The volume is made up to 96 litres

B.6 The mixture is cooled to room temperature.

C. Final Phase

C.1 728 g Na₂SeO₃ is added.

C.2 The pH is adjusted to 6,7 by adding NaOH (40% solution) or EDTA.

C.3 The volume is made up to 100 litres.

Example 3

Example 3 relates to a method to prepare a trace element solution predominantly to be used for cattle and includes the mineral elements Selenium and Copper.

The method enables preparation of 100 litres of the solution containing 40 mg Zn, 10 mg Mn, 5 mg Se and 15 mg Cu per ml.

A. Preparing MnCO₃

In a suitable container/drum, the MnCO₃ mud is prepared by adding solutions of 3600 g MnSO₄ and 4600 g Na₂CO₃ together. The mixture is decanted and wash three times.

Continuous Batch Process

To the MnCO₃ mud, hot water (70° C.) is added to a volume of at least 60 litres. The temperature at the start of the batch process is critical and should be at least 60° C.

B.1 Preparing MnEDTA 7840 g EDTA and 1960 g NaOH are weighed. The EDTA and NaOH are weighed. The EDTA/NaOH mixture is added to the drum, in small quantities to prevent excessive frothing, until the reaction is complete (leaving a clear pinkish solution).

B.2 Preparing ZnEDTA (2 steps)

Step 1:

10400 g EDTA, 2760 g NaOH and 2800 g ZnO are weighed. The EDTA and NaOH are mixed and the ZnO kept separate. The EDTA/NaOH mixture is added to the drum, in small quantities to prevent boiling over, followed by addition of the ZnO. The reaction is allowed to complete (again leaving a clear pink solution). The temperature at this stage could reach 103° C.

Step 2:

10400 g EDTA, 2760 g NaOH and 2800 g ZnO are weighed. The EDTA and NaOH are mixed and the ZnO kept separate. The EDTA/NaOH mixture is added to the drum, in small quantities to prevent boiling over, followed by addition of the ZnO. The reaction is allowed to complete (again leaving a clear pink solution). The temperature at this stage could reach 103° C.

B.3 Preparing CuEDTA 7040 g EDTA, 1848 g NaOH and 2780 g basic CuCO₃ are weighed. The EDTA and NaOH are mixed and the CuCO₃ kept separate. The EDTA/NaOH mixture is added to the drum, followed by careful addition of the CuCO₃, to prevent excessive frothing, and the reaction is allowed to complete (leaving a clear blue solution).

B.4 100 g chlorocresol is added and the mixture stirred till dissolved.

B.5 The mixture is made up to 96 litres

B.6 The mixture is allowed to cool to room temperature.

B. Final Phase

C.1 1212 g Na₂SeO₃ is added.

C.2 The pH is adjusted to 7,0 by adding NaOH (40% solution) or EDTA.

C.3 The volume is made up to 100 litres.

General

The invention therefore provides a trace element solution which is tissue friendly, i.e. is not damaging or irritant to the tissue of animals and which comprises selenium, copper, zinc, manganese, iron and chromium and at a concentration of the metals of at least 60 mg/ml. The trace elements in solution are in a scientifically formulated ratio according to the post-absorption requirements of the animals, calculated to provide, the following trace element solution example comprising:
(a) 35-50 mg/ml of zinc;
(b) 10-15 mg/ml manganese;
(c) 5-10 mg/ml selenium;
(d) 10-20 mg/ml copper;
(e) 5-10 mg/ml chromium;
(f) 5-50 mg/ml iron; and
(g) comprises 20-400 mg/ml iodine.

The iodine is provided in the form of potassium iodide or sodium iodide and the iron is provided in the form of iron chloride.

The method of preparing a trace element solution in accordance with the invention thus enables the production of a solution comprising an adequate trace mineral concentration so that a 5 to 10 ml injection can make a significant impact on the trace mineral status of the animal, i.e. a practically applicable injectable supplement and a product that can improve the trace mineral status of an animal is provided. This is important as livestock producers will only inject livestock if a real benefit can be demonstrated. Furthermore, the subcutaneous injection is the preferred route to minimize tissue damage.

What is claimed:

1. An injectable trace element solution, said solution comprising:
    (a) selenium;
    (b) zinc;
    (c) manganese; and
    (d) iron,
    wherein a total concentration of selenium, zinc, manganese and iron in the solution is at least 60 mg/ml.

2. The solution of claim 1, wherein the concentration of selenium in the solution is 5 to 10 mg/ml.

3. The solution of claim 1, wherein the concentration of zinc in the solution is 35 to 50 mg/ml.

4. The solution of claim 1, further comprising at least one of copper and chromium.

5. The solution of claim 1, further comprising at least one compound selected from the group consisting of iodine, potassium iodide, sodium iodide, iron chloride, zinc oxide, manganese sulphate, sodium selenite, copper carbonate, sodium carbonate, anhydrous disodium EDTA and sodium hydroxide.

6. The solution of claim 5, wherein at least one of the metals is provided in the form of an EDTA complex.

7. The solution of claim 6, wherein the EDTA complex is produced from at least one compound selected from the group consisting of sodium EDTA and potassium EDTA.

8. The solution of claim 1, further comprising chlorocresol as preservative.

9. The solution of claim 1, further comprising 5-10 mg/ml chromium.

10. The solution of claim 1, wherein the iron in solution is 5-50 mg/ml.

11. The solution of claim 1, further comprising 20-400 mg/ml iodine.

12. The solution of claim 1, wherein the selenium is present in an amount of 5 mg/ml.

13. The solution of claim 1, further comprising 5-10 mg/ml chromium.

* * * * *